United States Patent [19]

Takematsu et al.

[11] Patent Number: 4,517,381

[45] Date of Patent: May 14, 1985

[54] 2-METHYL-4'-ISOPROPYL-2-PENTENOYL ANILIDE

[75] Inventors: Tetsuo Takematsu, Utsunomiya; Mitihiko Nakaya, Mobara; Koichi Moriyasu, Yokohama; Nobuo Komoto, Mitaka, all of Japan

[73] Assignee: Mitsui Toatsu Chemicals, Inc., Tokyo, Japan

[21] Appl. No.: 629,605

[22] Filed: Jul. 11, 1984

[30] Foreign Application Priority Data

Jul. 19, 1983 [JP] Japan ................................. 58-130161

[51] Int. Cl.³ ................. C07C 102/04; C07C 102/06; C07C 103/133; A01N 9/20
[52] U.S. Cl. ........................................ 564/207; 71/118
[58] Field of Search ........................... 564/207; 71/118

[56] References Cited

U.S. PATENT DOCUMENTS

| | | | |
|---|---|---|---|
| 3,192,213 | 6/1965 | Krapcho | 564/207 X |
| 3,201,401 | 8/1965 | Krapcho | 564/207 X |
| 3,281,467 | 10/1966 | Wilson et al. | 564/207 |
| 3,852,058 | 12/1974 | Huffman | 564/207 X |
| 3,871,865 | 3/1975 | Teach | 564/207 X |
| 4,228,102 | 10/1980 | Besecke et al. | 564/207 X |
| 4,372,972 | 2/1983 | Chan | 564/207 X |

FOREIGN PATENT DOCUMENTS

| | | | |
|---|---|---|---|
| 2910976 | 10/1980 | Fed. Rep. of Germany | 564/207 |
| 0038755 | 3/1982 | Japan | 564/207 |
| 0142951 | 9/1982 | Japan | 564/207 |
| 0185246 | 11/1982 | Japan | 564/207 |
| 0032852 | 5/1983 | Japan | 564/207 |

*Primary Examiner*—Paul F. Shaver
*Attorney, Agent, or Firm*—Fisher, Christen & Sabol

[57] ABSTRACT

2-Methyl-4'-isopropyl-2-pentenoyl anilide, a selective herbicide comprising this compound as a main active ingredient, and a process for producing the aforesaid compound.

4 Claims, No Drawings

2-METHYL-4'-ISOPROPYL-2-PENTENOYL ANILIDE

This invention relates to 2-methyl-4'-isopropyl-2-pentenoyl anilide and a selective herbicide comprising this compound as a main active ingredient. The herbicide selectively controls noxious weeds by foliage application in the cultivation of gramineous crops including barley, wheat, oats, rye and corn. This invention also relates to a process for producing the aforesaid compound.

Known herbicides for barley, wheat, oats, rye and the like which have gained practical acceptance include, for example, alpha,alpha,alpha-trifluoro-2,6-dinitro-N,N-dipropyl-p-toluidine (U.S. Pat. No. 3,403,180; Treflan; trifluralin), 3-(3,4-dichlorophenyl)-1-methoxy-1-methylurea (U.S. Pat. No. 2,960,534; Afalon; linuron), 3-(3,4-dichlorophenyl)-1,1-dimethylurea (British Pat. No. 776,069; DCMU; diuron), S-2,3,3-trichloroallyl-N,N-diisopropylthiocarbamate (British Pat. No. 882,110; Avadex BW; triallate), 3-(2-benzothiazolyl)-1,3-dimethylurea (U.S. Pat. No. 2,756,135; Tribunil; methabenzthiazuron), methyl(±)-2-[4-(2,4-dichlorophenoxy)phenoxy]propionate (DE-OS No. 2,223,894; Hoelon; diclofopmethyl), etc. Known herbicides for corn and the like which have gained practical acceptance include, for example, 2-chloro-4-ethylamino-6-isopropylamino-s-triazine (Swiss Patent No. 329,277; atrazine), N-methoxymethyl-2,6-diethyl-alpha-chloroacetanilide (Dutch Patent Application No. 6,602,564; Lasso; alachlor), etc. Many of these herbicides, however, have been used only as pre-emergence soil treating agents since by foliar treatment, they have a low efficacy and causes phytotoxicity to crops. Generally, soil treating agents vary greatly in efficacy and phytotoxicity depending upon the soil conditions such as the nature of the soil, the content of organic matter, and its moisture content. Since all of the above-cited herbicides vary greatly in efficacy and phytotoxicity depending upon the soil conditions, they require care depending upon the soil conditions and sometimes their use is restricted. Furthermore, since these herbicides have a narrow herbicidal spectrum, it is difficult to control all noxious weeds by using them singly, and two or more of them should be used in combination. In addition, bcause these herbicides remain in the soil for a relatively long period of time, their phytotoxicity to another crop to be grown after harvesting gives rise to a problem, and sometimes, the amount of the herbicides should be restricted.

Besides the above-mentioned, various anilide derivatives as herbicides are known, and disclosed, for example, in C. W. Hoffman, et al., J. Agric. Food Chem., 8, 298 (1960) (3',4'-dichloropropionanilide; Stam; propanil), British Pat. No. 869,169 (Karsil or Solan), German Patent No. 1,166,547 (Potablan; monalide), U.S. Pat. No. 3,816,092, etc. These literature references, however, fail to give any description about the selectivity of these anilide derivatives for weeds occurring in the cultivation of barley, wheat, oats, rye and the like.

The present inventors have studied many compounds in order to develop a selective herbicide for gramineous crops, particularly barley, wheat, oats, rye, and corn. This study has led to the discovery that 2-methyl-4'-isopropyl-2-pentenoyl anilide shows a very broad herbicidal spectrum when applied to foliage, and has an excellent selective herbicidal action in that even when applied in very high concentrations, it does not cause any phytotoxicity to barley, wheat, oats, rye, corn, etc.

2-Methyl-4'-isopropyl-2-pentenoyl anilide of this invention is a novel compound. As a herbicide, this compound controls noxious weeds which are detrimental to almost all upland farms, and in particular, effectively controls highly noxious gramineous weeds such as wild oats (*Avena fatua* L.), Alopecurus species such as meadow foxtail (*Alopecurus pratensis* L.), black grass (*Alopecurus myosuroides*), and *Alopecurus aequalis* S., and low spear grass (*Poa annua* L.). On the other hand, it causes no phytotoxicity to barley, wheat, oats, rye and corn which are gramineous crops. Thus, the compound of this invention shows essential selectivity for foliage treatment and can be used very safely. Since it has a very small effect in soil treatment, its efficacy and phytotoxicity do not vary at all depending upon the soil conditions mentioned above.

The compound of this invention, 2-methyl-4'-isopropyl-2-pentenoyl anilide, can be easily prepared by reacting 4-isopropylaniline with 2-methyl-2-pentenoic acid, 2-methyl-2-pentenoyl chloride or 2-methyl-2-pentenoic anhydride, as schematically shown below.

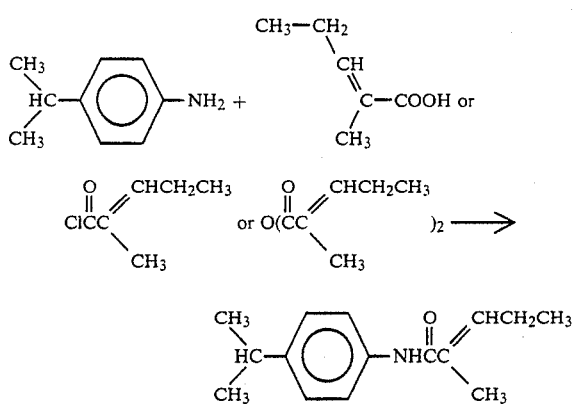

The reaction is carried out in an inert solvent such as benzene, toluene, xylene, ether, dioxane, tetrahydrofuran, methyl ethyl ketone, acetone or dimethylformamide. When the acid chloride or anhydride is used, an acid acceptor such as triethylamine, pyridine or potassium carbonate may be used as required. The reaction temperature may preferably be $-5°$ C. to $150°$ C. The reaction may also be carried out at the refluxing temperature. The reaction time, which varies depending upon the reaction temperature and the reagents used, is 0.5 to 10 hours.

2-Methyl-4'-isopropyl-2-pentenoyl anilide can also be easily synthesized as schematically shown below by reacting 4-isopropylaniline with a 2-halo-2-methyl-valeric acid, a 2-halo-2-methyl-valeryl chloride or a 2-halo-2-methylvaleric anhydride, and dehydrohalogenating the resulting 2-halo-2-methyl-4'-isopropylvaleranilide in the presence of a base.

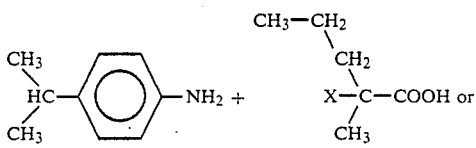

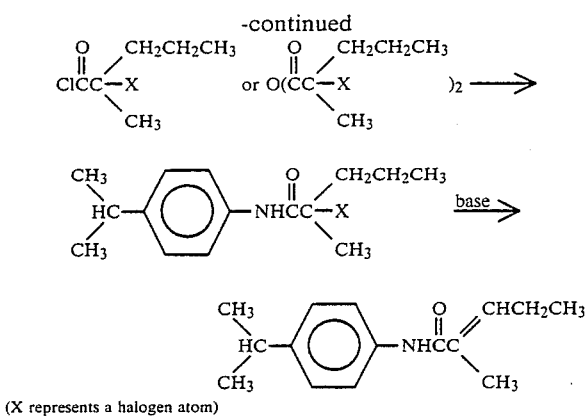

(X represents a halogen atom)

The dehydrohalogenation reaction is carried out in an organic base, or in a inert solvent in the presence of a base. Examples of the organic base are alpha-pipecoline, 2,6-dimethylpiperidine, 2-methylpyrrolidine, 2,5-dimethylpyrrolidine, pyridine, triethylamine, dimethylaniline and 1,8-diazabicyclo(5.4.0)-7-undecene. Examples of the inert solvent include benzene, toluene, xylene, ether, dioxane, tetrahydrofuran, methyl ethyl ketone, acetone and dimethylformamide. In addition to the organic base, an inorganic base in powder form such as potassium carbonate and sodium carbonate may be used. The reaction temperature is −10° to 150° C., preferably 10° to 70° C. The reaction time, which varies depending upon the reaction temperature or the reagents used, is 0.25 to 24 hours, preferably 0.5 to 2 hours.

Specifically, 2-methyl-4′-isopropyl-2-pentenoyl anilide is produced as shown in the following Synthesis Examples.

SYNTHESIS EXAMPLE I

To 20 ml of toluene were added 2 g (0.015 mole) of 4-isopropylaniline and 2 g (0.015 mole) of phosphorus trichloride. The mixture was heated to 60° C. with stirring. Subsequently, 1.7 g (0.015 mole) of 2-methylpentenoic acid was slowly added dropwise, and the mixture was stirred at 60° to 70° C. for 30 minutes. Toluene (100 ml) was freshly added, and the reaction mixture was washed with 130 ml of a saturated aqueous solution of sodium bicarbonate and 140 ml of hot water at 55° C. It was dried over anhydrous sodium sulfate, and concentrated by an evaporator to obtain 3.3 g of crude crystals. Recrystallization from benzene gave 2.7 g of 2-methyl-4′-isopropyl-2-pentenoyl anilide. m.p. 111.5°–113.5° C. IR $\nu_{max}^{cm-1}$ 3270, 1655 and 1625. Yield 77.9%.

SYNTHESIS EXAMPLE II 410 mg (3.04 mmoles) of 4-isopropylaniline was dissolved in 8 ml of m-xylene, and 500 mg of pyridine was added. With stirring under ice cooling, 440 mg (3.3 mmoles) of 2-methylpentenoyl chloride was added dropwise. After the addition, the mixture was stirred further at room temperature for 1 hour. The crystals that precipitated were separated by filtration, and the filtrate was concentrated. The residue was recrystallized from benzene to give 540 mg of 2-methyl-4′-isopropyl-2-pentenoyl anilide. m.p. 111.5°–113.5° C. IR $\nu_{max}^{cm-1}$ 3270, 1655 and 1625. Yield 76.9%.

SYNTHESIS EXAMPLE III (1) Synthesis of 2-bromo-2-methyl-4′-isoipropylvaleranilide 410 mg (3.04 mmoles) of 4-isopropylaniline was dissolved in 10 ml of benzene, and 500 mg of triethylamine was added. With stirring under ice cooling, 800 mg (4.10 mmoles) of 2-bromo-2-methylvaleryl chloride was added dropwise. After the addition, the mixture was further stirred at room temperature for 1 hour. The crystals that precipitated were separated by filtration. The filtrate was concentrated, and the residue was recrystallized from benzene to give 620 mg of 2-bromo-2-methyl-4′-isopropylvaleranilide. m.p. 87.2°–88.2° C. IR $\nu_{max}^{cm-1}$ 3300 and 1650. Yield 65.4%.

(2) Synthesis of 2-methyl-4′-isopropyl-2-pentenoyl anilide 620 mg of 2-bromo-2-methyl-4′-isopropylvaleranilide and 2 ml of alpha-pipecoline were added to 5 ml of acetone, and the mixture was stirred at 55° C. for 45 minutes. The crystals which precipitated were separated by filtration, and the filtrate was concentrated by an evaporator to give 450 mg (mp. 105.0°–107.5° C.) of crude crystals. Recrystallization from benzene gave 390 mg of 2-methyl-4′-isopropyl-2-pentenoyl anilide as crystals. m.p. 111.5°–113.5° C. IR $\nu_{max}^{cm-1}$ 3270, 1655 and 1625. Yield 84.9% (55.5% based on 4-isopropylaniline).

The rate of application of the compound of this invention can be arbitrary depending upon the degree of the need for inhibiting the growth of weeds. It is 0.1 to 10 kg per hectare as a standard and preferably 0.2 to 3 kg per hectare.

The herbicide of this invention comprises the compound of this invention as a main active ingredient. The compound of this invention, as it is, may be applied to a plant to be treated. Generally, however, a carrier and other adjuvants are mixed with the compound of this invention, and the mixture is formulated into forms generally used in the field of agricultural chemicals, for example dusts, emulsifiable concentrater, granules, wettable powders and flowable preparations.

Examples of the carrier are inorganic materials such as clays, talc, bentonite, calcium carbonate, diatomaceous earth, zeolite and silicic anhydride; vegetable organic materials such as wheat flour, soybean meal, starch and crystalline cellulose; polymeric compounds such as petroleum resins, polyvinyl chloride and polyalkylene glycols; urea; and waxes. Liquid carriers such as oils, organic solvents and water may also be used.

As the adjuvants, wetting agents, dispersants, stickers, spreaders, and the like may be used either singly or in combination as required.

Various surface-active agents, polymeric compounds such as gelatin, albumin, sodium alginate, methyl cellulose, carboxy methyl cellulose, polyvinyl alcohol and xanthan gum may be used as adjuvants for the purpose of wetting, dispersion, spreading, component stabilization, property stabilization, rustproofing, etc.

As desired, industrial fungicides (fungicidal and mold-proofing agents) may be added to flowable preparations in order to control fungi or molds.

The surface-active agents used may be non-ionic, anionic, cationic and amphoteric. Examples of preferred surface-active agents include polymerization products of ethylene oxide with alkylphenols, higher alcohols, alkylnaphthols, higher fatty acids, fatty acid esters or dialkylphosphoric acid amines, a polymer of ethylene oxide and propylene oxide, alkylsulfuric acid ester salts (e.g., sodium laurylsulfate), alkylsulfonic acid salts (e.g., sodium 2-ethylhexenesulfonate), and arylsulfonic acid salts (e.g., sodium ligninsulfonate, and sodium dodecylbenzenesulfonate).

The content of the compound of this invention as an active ingredient in the herbicide of this invention varies depending upon the form of the formulation, and is usually 1 to 20% by weight for dusts, 20 to 90% by weight for wettable powders, 1 to 30% by weight for granules, 1 to 50% by weight for emulsifiable concentrates, 10 to 90% by weight for flowable preparations and 20 to 70% by weight for dry flowable preparations. The amount of the adjuvants is 0 to 80% by weight, and the amount of the carrier is obtained by subtracting the contents of the active ingredient and the adjuvants from 100% by weight.

The herbicide of this invention may be used in admixture with at least one other herbicide, an agricultural chemical such as an insecticide, a fungicide or a plant growth controlling agent, a soil conditioner or a fertilizer compound, or may be formulated in combination with these. Sometimes, the combined use is expected to produce a synergistic effect.

Formulation Examples and Test Examples for herbicidal activity are shown below. The test results below demonstrate that the herbicide containing the compound of this invention shows a marked herbicidal efficacy in low dosages against all weeds tested, while it causes no phytotoxicity to gramineous crops (such as barley, wheat, oats, rye, corn) in high dosages. Thus, it has outstanding selectivity which surpasses comparative chemicals (Tribunil, Hoelon, Stam and Karsil).

FORMULATION EXAMPLE 1 (wettable powder)

Twenty parts by weight of the compound of this invention, 2 parts by weight of sodium alkylbenzenesulfonate, 2 parts by weight of polyoxyethylene alkyl phenyl ether and 76 parts by weight of Zieklite were well pulverized and mixed to form a wettable powder.

FORMULATION EXAMPLE 2 (wettable powder)

Thirty parts by weight of the compound of this invention, 6 parts by weight of polyoxyethylene alkyl phenyl ether ammonium sulfate, 2 parts by weight of a sodium naphthalenesulfonate/formaldehyde condensate, 1 part by weight of sodium alkylbenzenesulfonate, 2 parts by weight of polyvinyl alcohol and 59 parts by weight of diatomaceous earth were well pulverized and mixed to form a wettable powder.

FORMULATION EXAMPLE 3 (wettable powder)

Fifty parts by weight of the compound of this invention, 3 parts by weight of white carbon, 4 parts by weight of polyoxyethylene alkyl phenyl ether/ammonium sulfate, 2 parts by weight of sodium alkylbenzenesulfonate and 41 parts by weight of diatomaceous earth were well pulverized and mixed to form a wettable powder.

FORMULATION EXAMPLE 4 (wettable powder)

Fifty parts by weight of the compound of this invention, 5 parts by weight of white carbon, 4 parts by weight of polyoxyethylene alkyl phenyl ether ammonium sulfate, 2 parts by weight of sodium ligninsulfonate and 34 parts by weight of diatomaceous earth were well pulverized and mixed to form a wettable powder.

FORMULATION EXAMPLE 5 (wettable powder)

Eighty parts by weight of the compound of this invention, 5 parts by weight of white carbon, 7 parts by weight of polyoxyethylene alkyl phenyl ether ammonium sulfate, 2 parts by weight of a sodium naphthalenesulfonate/formaldehde condensate, 2 parts by weight of sodium alkylbenzenesulfonate and 4 parts by weight of diatomaceous earth were well pulverized and mixed to form a wettable powder.

FORMULATION EXAMPLE 6 (flowable preparation)

Water (76.7 parts by weight) was added to 20 parts by weight of the compound of this invention, 2 parts by weight of sodium ligninsulfonate, 0.3 part by weight of xanthan gum and 1 part by weight of polyoxyethylene alkyl aryl ether, and they were mixed. The mixture was finely pulverized by using a sand grinder to obtain a flowable preparation.

FORMULATION EXAMPLE 7 (flowable preparation)

Water (52.8 parts by weight) was added to 40 parts by weight of the compound of this invention, 3 parts by weight of a sodium naphthalenesulfonate/formaldehyde condensate, 2 parts by weight of sodium ligninsulfonate, 0.1 part by weight of xanthan gum, 0.1 part by weight of Deltop (organic iodine acetamide compound, industrial fungicide produced by Takeda Chemical Co., Ltd.) and 2 parts by weight of polyoxyethylene alkylaryl ether, and they were mixed. The mixture was then finely pulverized by using a sand grinder to form a flowable preparation.

FORMULATION EXAMPLE 8 (dust)

Three parts by weight of the compound of this invention, 3 parts by weight of sodium ligninsulfonate, 2 parts by weight of polyoxyethylene alkyl aryl ether and 92 parts by weight of clay were mixed and pulverized to form a dust.

FORMULATION EXAMPLE 9 (dust)

Twenty parts by weight of the compound of this invention, 5 parts by weight of sodium ligninsulfonate, 4 parts by weight of polyoxyethylene alkyl aryl ether and 71 parts by weight of clay were mixed and pulverized to form a dust.

FORMULATION EXAMPLE 10 (dry flowable preparation)

Sixty parts by weight of the compound of this invention, 5 parts by weight of sodium alkylbenzenesulfonate and 35 parts by weight of polypropylene glycol polyethylene glycol ether, and they were mixed. The mixture was finely pulverized by using a Jet-O-miser to form a dry flowable preparation.

FORMULATION EXAMPLE 11 (dry flowable preparation)

Seventy parts by weight of the compound of this invention, 2 parts by weight of sodium alkylbenzenesulfonate, 18 parts by weight of polypropylene glycol ethylene glycol ether and 10 parts by weight of white carbon were mixed, and the mixture was finely pulverized by using a Jet-O-miser to obtain a dry flowable preparation.

FORMULATION EXAMPLE 12 (granules)

20.5 Parts by weight of the finely pulverized compound of this invention, 2.0 parts by weight of Gohsenol GL-05S (polyvinyl alcohol manufactured by Nihon Synthetic Chemical Co., Ltd.) 2.0 parts by weight of Sunexs P-252 (sodium ligninsulfonate made by Sanyo Kokusaku Pulp Co., Ltd.) and 75.5 parts by weight of clay were well mixed, and a suitable amount of water was added to wet the mixture. The mixture was then extruded and granulated by an injection molding machine. The granules were air-dried at 60 to 90° C. to break the granules, and their size was adjusted to 0.3 to 1 mm by a size adjusting machine to form granules.

FORMULATION EXAMPLE 13 (granules)

Five parts by weight of the finely pulverized compound of the invention, 72 parts by weight of bentonite, 20 parts by weight of talc, 2 parts by weight of calcium dodecylbenzenesulfonate and 1 part by weight of calcium ligninsulfonate were well mixed, and a suitable amount of water was added to wet the mixture. The mixture was then extruded by an injection molding machine to form granules. The granules were air-dried at 60° to 90° C., broken and then adjusted in size by a size adjusting machine to 0.5 to 1.2 mm to form granules.

FORMULATION EXAMPLE 14 (granules)

Twelve parts by weight of the finely pulverized compound of this invention, 60 parts by weight of bentonite, 25 parts by weight of talc, 2 parts by weight of a sodium naphthalensulfonate/formaldehyde condensate, and 1 part by weight of dioctyl sulfosuccinate were well mixed, and the mixture was wetted with a suitable amount of water. The wet mixture was extruded by an injection molding machine to form granules. The granules were air-dried at 60 to 90° C. to break them. The broken particles were adjusted to a size of 0.3 to 1 mm by a size adjusting machine to form granules.

TEST EXAMPLE 1

Test for activity by foliage treatment:

Upland farm soil (3 kg) was filled in each of plastic Wagner pots having a capacity of a/5,000, and 0.8 g of each of $N_2$, $P_2O_5$ and $K_2O$ were applied to the entire layer. Predetermined amounts of seeds of various crops and weeds were sown, and covered with soil to a depth of 0.5 to 1 cm. The pots were placed in a greenhouse to allow the plants to germinate and grow. In the 2- to 3-leaf stage of the crops and the weeds, a predetermined amount of a wet-table powder prepared as in Formulation Example 1 was sprayed on all over the plants. On the 21st day after the application of the chemical, the effects of the chemical on the crops and weeds were observed and examined. The results are shown in Table 1.

TABLE 1

| Test Compound | Concentration of the active component (%) | A | B | C | D | E | F | G | H | I | J | K | L |
|---|---|---|---|---|---|---|---|---|---|---|---|---|---|
| Compound of the invention | 1.0 | 0 | 0 | 0 | 0 | 5 | 5 | 5 | 5 | 5 | 5 | 5 | 5 |
|  | 0.5 | 0 | 0 | 0 | 0 | 5 | 5 | 5 | 5 | 5 | 5 | 5 | 5 |
|  | 0.25 | 0 | 0 | 0 | 0 | 5 | 5 | 5 | 5 | 5 | 5 | 5 | 5 |
|  | 0.125 | 0 | 0 | 0 | 0 | 4 | 5 | 5 | 5 | 5 | 5 | 5 | 4.5 |
| Karsil (control) (*1) | 0.5 | 5 | 5 | 5 | 5 | 5 | 5 | 5 | 5 | 5 | 5 | 5 | 5 |
|  | 0.25 | 5 | 4 | 4 | 4 | 4 | 5 | 5 | 5 | 5 | 5 | 5 | 4 |
|  | 0.125 | 3 | 3 | 3 | 3 | 3.5 | 5 | 5 | 5 | 5 | 5 | 5 | 3 |

Note
(*1): Karsil: 2-methyl-3',4'-dichlorovaleranilide
(*2): Degree of injury to assay plants: The phytotoxicity and the degree of injury are shown by the following scale.

| Rating | Degree of injury (%) | State of phytotoxicity |
|---|---|---|
| 5 | 100 | Withered (complete control in the case of weed seeds) |
| 4 | 80 | Severe (80% control) |
| 3 | 60 | Moderate (60% control) |
| 2 | 40 | Small (40% control) |
| 1 | 20 | Slight (20% control) |
| 0 | 0 | No injury (no control) |

The abbreviations for the plants' names were as follows:

A: Wheat (Triticum)
B: Rye (Secale cereale)
C: Oats (Avena sativa)
D: Barley (Hordeum vulgare)
E: Japanese millet (Echinochloa frumentacea)
F: Large crabgrass (Digitaria ciliaris)
G: Green amaranth (Amaranthus viridis L.)
H: Cocklebur (Xanthium strumarium)
I: Morning glory (Ipomea purpurea)
J: Velvet leaf (Abutilon theophrasti)
K: Oriental senna (Cassia obtusifolia)
L: Black grass (Alopecurus myosuroides)

TEST EXAMPLE 2

Weed controlling test in the growing period in an upland farm:

Soil was filled in planters having a capacity of a/1,000, and seeds of wheat, wild oats, Alopecurus species (meadow foxtail, black grass and water foxtail), low spear grass, pick purse (Capsella bursapostoris Medic), cleavers (Galium spurium), lamb's quarters (Chenopodium album) and chickweed (Stellaria media) were sown, and grown in a greenhouse. When the test plants grew to a 2- to 3-leaf stage, a predetermined amount of a flowable preparation, prepared as in Formulation Example 6, was diluted with water in an amount corresponding to 10 liters per are and sprayed by a microsprayer. Thirty days after the treatment, the staate of growth of the crops and weeds was examined. The results are shown in Table 2. The degree of phytotoxicity to the crops and the herbicidal efficacy on the weeds were evaluated on the following scale by comparing the growth condition (the air dry weight) of the crops or weeds in a treated area with that in a non-treated area.

TABLE 2

| Rating | Survival rate relative to the non-treated area |
|---|---|
| 0 | 91–100% |
| 1 | 61–90% |
| 2 | 36–60% |
| 3 | 11–35% |
| 4 | 6–10% |
| 5 | 0–5% |

TABLE 2-continued

| Test Compound | Amount of the active ingredient (g/a) | Crop A | Weed M | N | L | O | P | Q | R | S | T |
|---|---|---|---|---|---|---|---|---|---|---|---|
| Compound of the invention | 5 | 0 | 4 | 5 | 4 | 4 | 5 | 4 | 4 | 3 | 4 |
| | 10 | 0 | 5 | 5 | 4 | 4 | 5 | 5 | 5 | 4 | 5 |
| | 20 | 0 | 5 | 5 | 5 | 5 | 5 | 5 | 5 | 5 | 5 |
| | 30 | 0 | 5 | 5 | 5 | 5 | 5 | 5 | 5 | 5 | 5 |
| Tribunil (control) (*1) | 10 | 0 | 0 | 0 | 0 | 0 | 0 | 4 | 3 | 5 | 4 |
| | 20 | 0 | 0 | 0 | 0 | 0 | 1 | 5 | 4 | 5 | 5 |
| | 30 | 0 | 0 | 1 | 1 | 1 | 1 | 5 | 4 | 5 | 5 |
| Hoelon (control) (*2) | 5 | 0 | 4 | 4 | 2 | 3 | 4 | 0 | 0 | 0 | 0 |
| | 10 | 0 | 5 | 5 | 3 | 4 | 5 | 0 | 0 | 0 | 0 |
| | 20 | 1 | 5 | 5 | 5 | 5 | 5 | 0 | 0 | 0 | 0 |

(*1): 3-(2-Benzothiazolyl)-1,3-dimethylurea (methabenzthiazuron)
(*2): Methyl(±)-2-[4-(2,4-dichlorophenoxy)-phenoxy]propionate (diclofopmethyl)

The abbreviations for the plants' names are as follows:
A: Wheat (Triticum)
M: Wild oats (Avena fatua L.)
N: Meadow foxtail (Alopecurus pratensis L.)
L: Black grass (Alopecurus myosuroides)
O: Water foxtail (Alopecurus aequalis)
P: Low spear grass (Poa annua L.)
Q: Pick purse (Capsella bursapastoris Medic)
R: Cleavers (Galium spurium)
S: Chickweed (Stellaria media)
T: Lamb's quarters (Chenopodium album)

TEST EXAMPLE 3

Weed controlling test in the growth period in an upland farm:

Soil was filled in planters having a capacity of a/1000, and seeds of barnyard grass (Echinochloa oryzicola), large crabgrass (Digitaria ciliaris), green foxtail (Steria viridis), Johnson grass (Sorghum halepense), lamb's quarters, green amaranth, cocklebur, morning glory, velvet leaf and corn were sown, and grown in a greenhouse.

When the test plants grew to a stage of 1.5 to 2.5 leaves, a predetermined amount of a wettable powder, prepared as in Formulation Example 1, was diluted with water in an amount corresponding to 10 liters per are, and sprayed by a micro pressure sprayer. Thirty days after the treatment, the states of growth of the crops and weeds were examined, and the results shown in Table 3 were obtained. The degree of phytotoxicity and the herbicidal efficacy on the weeds are shown by the same method as in Test Example 2.

TABLE 3

| Test Compound | Amount of the active ingredient (g/a) | Crop U | Weed V | F | W | X | T | G | H | I | J |
|---|---|---|---|---|---|---|---|---|---|---|---|
| Compound of the invention | 2 | 0 | 3 | 4 | 4 | 4 | 5 | 5 | 5 | 4 | 5 |
| | 5 | 0 | 4 | 5 | 5 | 5 | 5 | 5 | 5 | 5 | 5 |
| | 10 | 0 | 5 | 5 | 5 | 5 | 5 | 5 | 5 | 5 | 5 |
| | 20 | 1 | 5 | 5 | 5 | 5 | 5 | 5 | 5 | 5 | 5 |
| Stam (control) (*1) | 2 | 2 | 3 | 4 | 4 | 3 | 5 | 3 | 3 | 2 | 2 |
| | 5 | 2 | 4 | 5 | 5 | 4 | 5 | 4 | 4 | 4 | 3 |
| | 10 | 3 | 5 | 5 | 5 | 4 | 5 | 5 | 5 | 5 | 5 |
| | 20 | 3 | 5 | 5 | 5 | 5 | 5 | 5 | 5 | 5 | 5 |

(*1): 3',4'-Dichloropropionanilide (propanil), popularly called DCPA.

The abbreviations for the plants are as follows:
U: Corn (Zea mays L.)
V: Barnyard grass (Echinochloa oryzicola)
F: Large crabgrass (Degitaria ciliaris)
W: Green foxtail (Steria viridis)
X: Johnson grass (Sorghum halepense)
T: Lamb's quarters (Chenopodium album)
G: Green amaranth (Amaranthus viridis L.)
H: Cocklebur (Xanthium strumarium)
I: Morning glory (Ipomea purpurea)
J: Velvet leaf (Abutilon theophrasti)

What is claimed is:

1. 2-Methyl-4'-isopropyl-2-pentenoyl anilide.

2. A selective herbicide comprising 2-methyl-4'-isopropyl-2-pentenoyl anilide as an active ingredient.

3. A process for producing 2-methyl-4'-isopropyl-2-pentenoyl anilide, which comprises reacting 4-isopropylaniline with 2-methyl-2-pentenoic acid, 2-methyl-2-pentenoyl chloride or 2-methyl-2-pentenoic anhydride.

4. A process for producing 2-methyl-4'-isopropyl-2-pentenoyl anilide, which comprises reacting 4-isopropylaniline with a 2-halo-2-methyl-valeric acid, a 2-halo-2-methyl-valeryl chloride or a 2-halo-2-methyl-valeric anhydride, and dehydrohalogenating the resulting 2-halo-2-methyl-4'-isopropylvaleranilide in the presence of a base.

* * * * *